United States Patent
Mason et al.

[11] Patent Number: 5,241,951
[45] Date of Patent: * Sep. 7, 1993

[54] THERAPEUTIC NONAMBIENT TEMPERATURE FLUID CIRCULATION SYSTEM

[75] Inventors: Bradley R. Mason, Olivenhain; Jeffrey T. Mason, Escondido, both of Calif.

[73] Assignee: Breg, Inc., Vista, Calif.

[*] Notice: The portion of the term of this patent subsequent to Jan. 14, 2009 has been disclaimed.

[21] Appl. No.: 767,494

[22] Filed: Sep. 30, 1991

Related U.S. Application Data

[63] Continuation-in-part of Ser. No. 578,508, Sep. 5, 1990, Pat. No. 5,080,089.

[51] Int. Cl.$^5$ .............................................. A61H 9/00
[52] U.S. Cl. ..................................... 607/104; 607/108
[58] Field of Search ............... 128/24 R, 24.1, 399, 128/400, 402, 68.1, 77, 82.1, 89 R, 384, DIG. 20, 594

[56] References Cited

U.S. PATENT DOCUMENTS

| | | | |
|---|---|---|---|
| 267,435 | 11/1982 | Leiter . | |
| 2,726,658 | 12/1955 | Chessey | 128/400 |
| 2,930,594 | 3/1960 | MacCracken | 257/306 |
| 3,091,242 | 5/1963 | Johnson et al. | 128/402 |
| 3,425,419 | 2/1969 | Dato | 128/400 |
| 4,149,529 | 4/1979 | Copeland et al. | 128/24.1 |
| 4,335,726 | 6/1982 | Kolstedt | 128/400 |
| 4,459,468 | 7/1984 | Bailey | 128/400 |
| 4,691,762 | 9/1987 | Elkins et al. | 165/46 |
| 4,821,354 | 4/1989 | Little | 5/422 |
| 4,962,761 | 10/1990 | Golden | 128/400 |
| 5,080,089 | 1/1992 | Mason et al. | 128/402 |

FOREIGN PATENT DOCUMENTS 0039443 4/1981 European Pat. Off. .

Primary Examiner—Robert Bahr
Attorney, Agent, or Firm—Rodney F. Brown

[57] ABSTRACT

A device is provided for therapeutically treating a desired region of a patient's body with a nonambient temperature fluid which is circulated through a pad having a tortuous fluid pathway which is positioned on the treatment region. The device has fluid inlet and outlet lines, each having an end connected to the pad and an opposite end positioned in a reservoir containing the nonambient temperature fluid, thereby providing fluid communication between the pad and the reservoir, and enabling continuous circulation of the fluid therebetween. Fluid drive is provided by a submersible pump at the end of the fluid inlet line in the reservoir. Temperature control of the pad is enabled by an in-line valve and temperature monitor positioned in the outlet line.

19 Claims, 2 Drawing Sheets

THERAPEUTIC NONAMBIENT TEMPERATURE FLUID CIRCULATION SYSTEM

This application is a continuation-in-part patent application of our prior co-pending patent application, "Therapeutic Apparatus Applying Compression and a Nonambient Temperature Fluid," Ser. No. 578,508 filed on Sep. 5, 1990, now U.S. Pat. No. 5,030,089.

TECHNICAL FIELD

The present invention relates generally to therapeutic treatment of the body. The present invention particularly relates to an apparatus for treating bodily injuries and ailments by cooling or heating the affected body surface. The present invention more particularly, though not exclusively, relates to an apparatus for continuously circulating a nonambient temperature fluid across a desired treatment surface of the body.

BACKGROUND OF THE INVENTION

Bodily injuries and ailments are commonly treated by applying a nonambient temperature material to the affected area of the body. For example, a low temperature material, typically applied in the form of ice or a cold liquid, advantageously inhibits swelling in the region of the injury. A high temperature material, typically applied in the form of hot water or an active heating element, advantageously reduces pain and promotes healing. A number of splint devices are known in the art for applying nonambient temperature materials to injured or otherwise ailing areas of the body as evidenced by U.S. Pat. Nos. 3,548,819 to Davis et al; 3,901,225 to Sconce; and 4,706,658 to Cronin. One disadvantage of such devices is that the low temperature materials become warmer as they remain in contact with the body during treatment and the body transfers heat thereto. Conversely, high temperature materials become cooler as they transfer heat to the body. This disadvantage can be remedied by periodically replacing the nonambient temperature materials. However, constant replenishment of these materials is cumbersome and inconvenient, and results in periodic treatment temperature fluctuations.

In response to this problem, a number of systems have been developed for continuously circulating a cooling fluid from a low temperature reservoir to a desired body location. Such systems are typified by U.S. Pat. Nos. 2,726,658 to Chessey; 3,683,902 to Artemenko et al; and 4,962,761 to Golden. These systems are noteworthy in that they are relatively complex and thus, costly to manufacture and maintain, as well as being somewhat difficult to operate. Accordingly, the systems are not particularly practical for use among the general population.

Given the proliferation of sports and leisure activities and the proliferation of injuries associated therewith, a widespread need exists for a practical therapeutic nonambient temperature treatment device. In particular, a need exists for a device which circulates a nonambient temperature fluid across a desired surface of the body to provide therapeutic treatment thereto, wherein the device is relatively simple to operate and inexpensive to produce and maintain. As such a therapeutic nonambient temperature treatment device is needed which can be employed in the home or in the workplace to provide cost-effective treatment which does not significantly disrupt the daily schedule of the user.

SUMMARY OF THE INVENTION

The present invention is a device for therapeutically treating a desired region of a patient's body with a nonambient temperature fluid, i.e., a cooling fluid or a heating fluid, which is circulated through a pad placed over the desired region. The pad encloses a continuous tortuous flowpath for the nonambient temperature fluid which has a fluid inlet port at its entrance and a fluid outlet port at its exit. Corresponding fluid inlet and outlet lines are provided, each having an end connected to the inlet and outlet ports respectively. The opposite ends of the fluid inlet and outlet lines are placed in a nonambient temperature reservoir containing an excess of nonambient temperature fluid, thereby providing fluid communication between the pad and the reservoir, and enabling circulation of the fluid therebetween.

The end of the inlet line situated in the reservoir has a pump positioned thereon which is submersed in the fluid to provide a drive mechanism for the fluid. Thus, fluid circulation is effected by pumping the fluid from the reservoir through the inlet line into the pad via the inlet port. The fluid follows a tortuous flowpath through the pad to the outlet port where it is discharged back to the reservoir through the outlet line.

To provide for temperature control of the pad, an in-line valve is positioned in either the inlet or outlet line, but preferably the outlet line. The valve is an adjustable flow restrictor, which enables regulation of the fluid flow rate through the system. In the case of a cooling fluid, by closing the valve to reduce the flow rate of fluid through the system, the fluid residence time in the pad increases, correspondingly increasing the temperature in the pad due to heat transfer effects from the body. By opening the valve to increase the flow rate, the cooling fluid residence time in the pad decreases causing a temperature decrease therein. Conversely, in the case of a heating fluid, closing the valve decreases the temperature in the pad, while opening the valve increases the temperature in the pad. An in-line temperature monitor is further provided, preferably in the outlet line, to enable operator monitoring of the fluid temperature in the pad. The in-line valve may accordingly be adjusted in response to temperature readings from the monitor.

The temperature monitor and flow restriction valve may be enclosed within a unitary control housing. A manual valve control knob and a temperature display are operator accessible on the exterior of the housing. An electrical connector can also be provided on the exterior of the housing which is connected to an internal power line extending to the pump. The connector enables electrical connection of the pump to an external power source, such as a battery or a conventional wall outlet, via an external power line. Alternatively, the device may have its own internal power source in the form of a battery.

A joint comprising a pair of inlet and outlet couplings is provided to connect the fluid inlet and outlet lines and the fluid inlet and outlet ports, respectively. The joint enables dissociation of the pad from the lines and allows interchangability or removal of the pad for storage or cleaning. An insulative sheath may be provided along the length of the inlet and outlet lines which, in association with the control housing, fully encloses the lines within a single tubular unit for ease of handling and for temperature insulation of the lines. The internal power line may further be included within the tubular unit extending from the housing to the pump.

The device as described above is designed to be portable to the extent it is readily transportable for set up and use at varied locations. The nonambient temperature reservoir may be structurally dissociable from the remainder of the device so that it need not be transported with the device to each location of use, thereby enhancing the portability of the device. A conventional bucket or insulated passive cooler may be used as the reservoir, both of which are commonly available at most locations. One need only fill the reservoir with a nonambient fluid, such as ice water or hot water, and connect the power source to render the device operable. If the device is used for cooling and the reservoir becomes too warm, it can be restored to a low temperature simply by adding ice as desired. Likewise, if the device is used for heating and the reservoir becomes too cool, hot water can be added.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
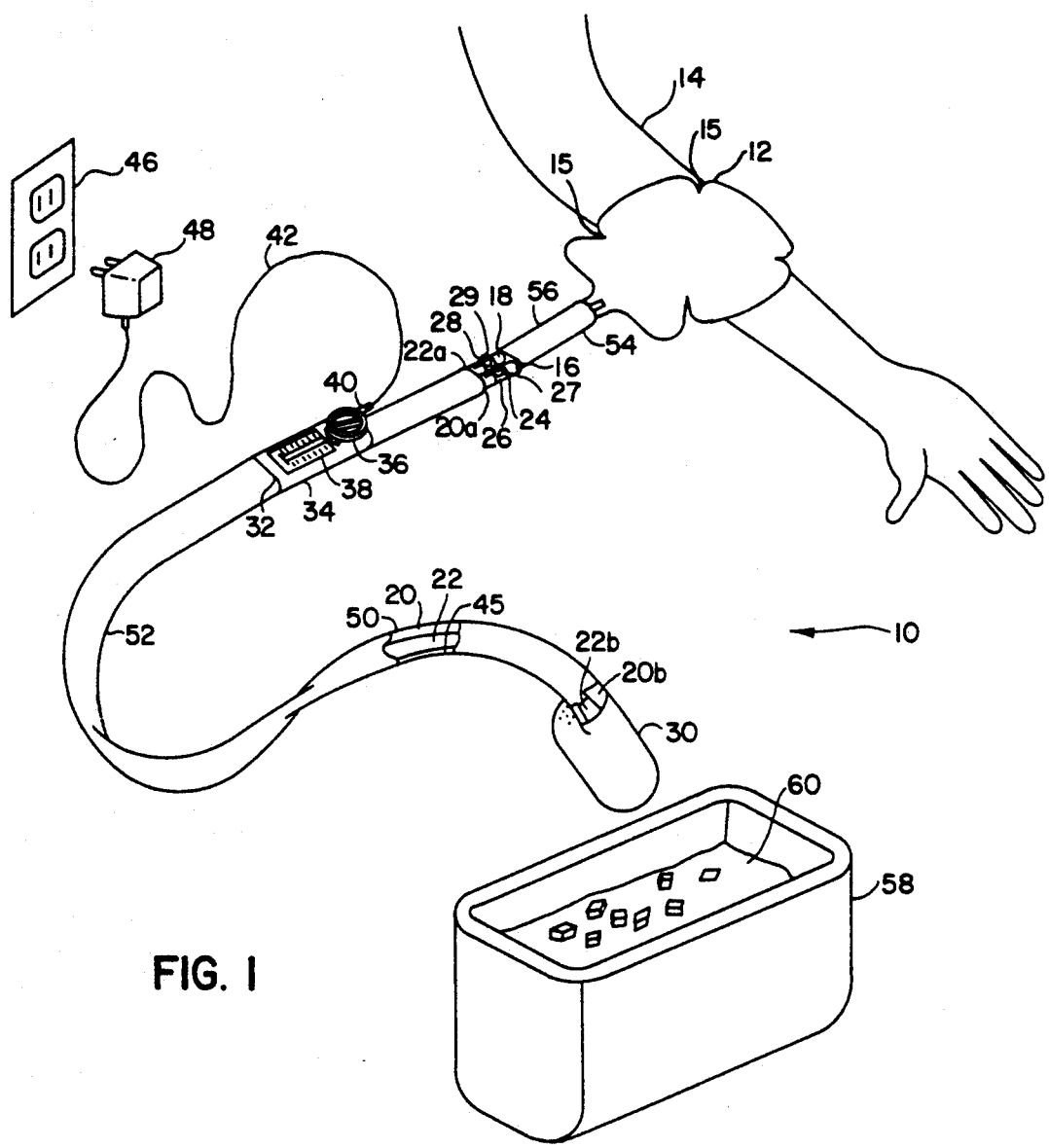
FIG. 1 is a perspective view of the fluid circulation system of the present invention.

Referring initially to FIG. 1, the fluid circulation system of the present invention is shown and generally designated as 10. For purposes of illustration, FIG. shows a low temperature embodiment of the fluid circulation system of the present invention which is generally designated as 10. It is understood, however, that the description of system 10 as shown and set forth below applies generally to high temperature embodiments of the present invention as well.

Referring to FIG. 1, system 10 comprises a cooling pad 12 positionable on the body of a patient at the point where therapeutic low temperature treatment is desired. Pad 12 is shown here on the arm 14, but it is apparent that pad 12 can be positioned substantially anywhere on the body where treatment is desired. Pad 12 is preferably fabricated from a pliable polyurethane film such that it is at least somewhat conformable to the body contours of the patient. To facilitate conformance, pad 12 has a plurality of seams 15 formed therein.

Pad 12 has a fluid inlet port 16 and a fluid outlet port 18 which are connected to a fluid inlet line 20 and a fluid outlet line 22, respectively. Lines 20, 22 and ports 16, 18 have substantially the same inside diameter of about 3/16 inches and are connected at joint 24 having two snap-action locking couplings 26 and 28 having lock release buttons 27 and 29. More specifically, fluid inlet port 16 is connected to the proximal end 20a of fluid inlet line 20 across inlet coupling 26, and fluid outlet port 18 is connected to the proximal end 22a of fluid outlet line 22 across outlet coupling 28.

Each coupling 26, 28 comprises a male connector on the port side of the coupling and a female connector on the line side of the coupling. The male connectors of couplings 26, 28 are housed together in a unitary molded mount, and the female connectors are similarly housed in a unitary mount to facilitate simultaneous connection of couplings 26, 28. Couplings 26, 28 are further provided with an internal shut off valve which automatically closes lines 20, 22 and ports 16, 18 when the couplings are disconnected.

System 10 further comprises a pumping unit 30 and a control unit 32. Pumping unit 30 is connected to fluid inlet and outlet lines 20, 22 at distal ends 20b, 22b thereof. Control unit 32 is integral with lines 20, 22, and has a housing 34 having a manually adjustable valve control knob 36 and a temperature display 38 mounted thereon. Housing 34 also has an electrical connector 40 mounted thereon which enables an electrical connection between pumping unit 30 and an external power source. Specifically, electrical connection is provided by an external power line 42 which is connected at one end to an internal power line 44 (shown in FIG. 3) across electrical connector 40 and which is connected at the other end to a conventional ac current wall plug 46 across a transformer 48. Internal power line 44 is positioned within a waterproof conduit 45 which extends from control unit 32 to pumping unit 30.

System 10, as shown, is reliant on an external ac current power source which limits its portability. As an alternate external power source to conventional ac current, a portable external battery pack (not shown) may be provided consisting of disposable dry D-cell batteries or rechargeable batteries. External power for system 10 may also be obtained from an automobile battery by providing an adaptor line (not shown) from connector 40 which fits into an automobile cigarette lighter outlet.

System 10 may be rendered more portable by eliminating electrical connector 40 external power cord 42, and transformer 48 and replacing them with an internal power pack (not shown) in control unit 32 which is connected to internal power line 44. Alternatively, electrical connector 40, external power cord 42, and transformer 48 may be retained in parallel with an internal power pack to provide system 10 with the capability of utilizing either an external or internal power source.

An insulative sheath 50 is provided over cooling fluid inlet and outlet lines 20, 22 and conduit 45 which, in conjunction with control unit housing 32, forms a substantially water-proof tubular unit 52 containing lines 20, 22 and conduit 45 from junction 24 to pump unit 30. Sheath 50 as well as lines 20, 22 and conduit 45 are formed from flexible materials which render tubular unit 52 fully flexible. Sheath 50 has a strong and resilient plastic exterior skin and an insulating foam interior which minimizes heat exchange between lines 20, 22 and the ambient atmosphere and further prevents condensate formation on the exterior of lines 20, 22. A flexible sheath 54 having a similar composition may also be provided over inlet and outlet ports 16, 18 extending between junction 24 and pad 12 to form a tubular unit 56 for ports 16, 18.

System 10 has a low temperature reservoir 58 which as shown is structurally independent of the remainder of system 10 such that pump unit 30 and distal ends 20b, 22b of lines 20a, 22a are freely positionable within reservoir 58. Alternatively, reservoir 58 can be structurally integral with system 10 by connecting line 20, 22 thereto. Reservoir 58 may be substantially any externally-accessible hollow fluid container, such as a bucket or a tub, although it is preferably an insulated container, such as a conventional insulated picnic cooler having a cover (not shown) for maintaining the low temperature therein. Cooling fluid 60, which is a fluid cooled below ambient room temperature and preferably ice water, is retained within reservoir 58.

Figure 2:
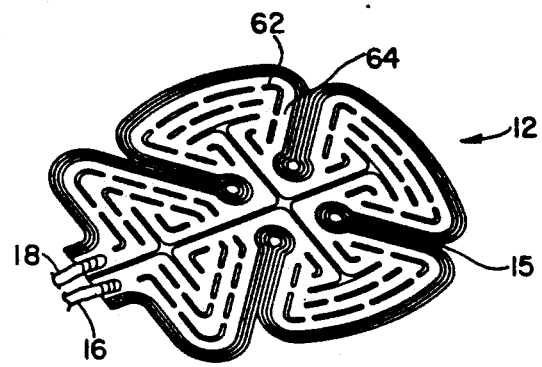
FIG. 2 is a view of the interior of the pad in the fluid circulation system of the present invention.

FIG. 2 shows the interior baffle pattern of cooling pad 12, wherein the polyurethane outer shell of pad 12 has been removed for purposes of illustration. Pad 12 contains a plurality of baffles 62 which are arranged to provide a tortuous flowpath 64 for cooling fluid 60 entering pad 12 via inlet port 16, and exiting pad 12 via outlet port 18. It is noted that baffles 62 engage the outer shell of pad 12 both at their tops and bottoms to prevent short-circuiting of baffles 62, thereby forcing cooling fluid 60 to flow around baffles 62 in a tortuous manner.

Figure 3:
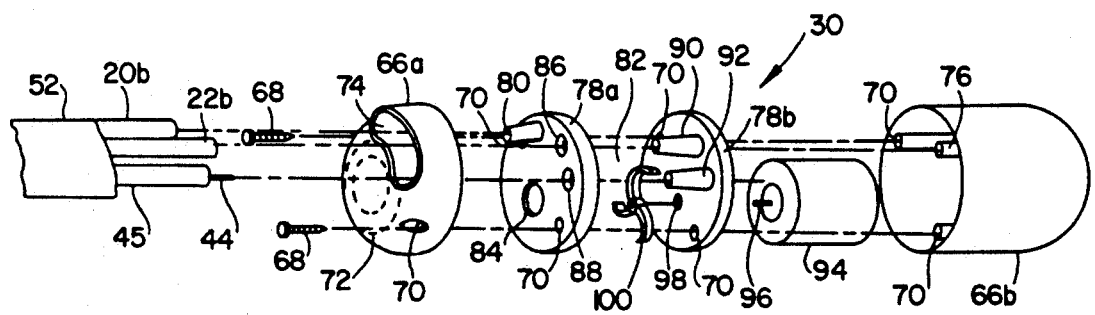
FIG. 3 is an exploded view of the pump unit in the fluid circulation system of the present invention.

FIG. 3 shows pump unit 30 in detail. Pump unit 30 comprises a pump housing 66 having a top portion 66a and a bottom portion 66b which are held together by screws 68 fitting into screw holes 70. Top housing portion 66a has a pump inlet port 72 which is perforated to allow fresh cooling fluid 60 to pass therethrough from reservoir 58, while blocking large solid particles, such as crushed ice, from passing therethrough. Top housing portion 66a also has an opening 74 formed therein to receive tubular unit 52 containing inlet and outlet lines 20, 22 and conduit 45. Bottom housing portion 66b has a pump outlet port 76 which receives cooling fluid from pad 12 via outlet line 22 and discharges it to reservoir 58.

Internal to housing 66 are upper plate 78a and lower plate 78b. Upper plate 78a has a nozzle so formed therein which provides fluid communication between distal end of inlet line 20b and pumping chamber 82. The space between plates 78a and 78b define chamber 82. Upper plate 78a also has a cooling fluid inlet passageway 84, outlet line opening 86, and power line opening 88 formed therethrough. Lower plate 78b has a nozzle 90 formed therein which provides fluid communication between distal end of outlet line 22b and pump outlet port 76. Lower plate 78b is further provided with a nipple 92 through which line 45 passes to pump motor 94 disposed within bottom housing portion 66b. Lower plate 78b is water-tight to prevent intrusion of water into motor 94. Pump motor 94 has a drive shaft 96 extending into pumping chamber 82 via shaft opening 98 formed through lower plate 78b. Shaft 96 connects to an impeller blade 100 disposed within chamber 82.

METHOD OF OPERATION

The fluid circulation system 10 of the present invention is operated by filling low temperature reservoir 58 with ice water 60, which is at a temperature approaching the freezing point of water, and covering reservoir 58 to maintain the fluid temperature therein. With joint 24 secured, pad 12 is placed on the skin of the patient at the point on the body where therapeutic treatment is desired. An additional padding material, such as a soft cloth, may be placed on the skin between the pliable surface of pad 12 and the skin for the comfort of the patient.

Pump unit 30 is submerged in the ice water 60 and external power line 42 is connected to a power source to activate the pump motor 94. Fresh ice water 60 is drawn from reservoir 58 into pumping chamber 82 and driven by impeller blade 100 through inlet line 20 and inlet port 16 into pad 12. The ice water travels the entirety of flowpath 64 and exits pad 12 via outlet port 18. The ice water is returned to reservoir 58 via outlet line 22 and pump outlet port 76.

This fluid circulation cycle is performed continuously for the duration of the desired treatment period. Temperature control of pad 12 during the circulation cycle is achieved by manually adjusting a conventional flow restrictor valve, which is preferably integral with control unit 32 and positioned across outlet line 22. The valve is adjusted by means of valve control knob 36 on control unit 32. By turning knob 36 in a direction to restrict flow through line 22, the temperature of pad 12 is increased, and conversely by turning knob 36 in the opposite direction to increase flow through line 22, the temperature of pad 12 is decreased. If the ice in reservoir 58 becomes depleted, additional amounts of ice may be added as needed. The valve of control unit 32 further acts to regulate the back pressure in system 10 as a function of the size of the valve opening.

Temperature control is facilitated by the temperature display 38 on the control unit 32 which is in communication with a temperature measuring means. The temperature measuring means and display 38 are preferably provided in the form of a conventional liquid thermometer which is positioned in outlet line 22. Termination of the circulation cycle is enabled simply by disconnecting the external power line 42 from the power source.

The high temperature embodiment of system 10 is primarily distinguishable from the low temperature embodiment described above in that a heated fluid is substituted for the cooling fluid. The heated fluid is preferably water which is heated to a temperature above room temperature, i.e., exceeding ambient. The temperature of the pad containing the heated fluid may be decreased by partially closing the valve across the outlet line to diminish flow therethrough, while the temperature of the pad may be increased by opening the valve to increase the flow.

While the particular Therapeutic Nonambient Temperature Fluid Circulation System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A device for therapeutically treating a desired portion of the body of a patient with a nonambient temperature fluid comprising:
   a pad positionable on the desired portion of the body, said pad having a fluid inlet port, a fluid outlet port, and a continuous fluid flowpath through said pad from said inlet port to said outlet port for circulation of a nonambient temperature fluid;
   a fluid inlet line having two ends, a first inlet end in fluid communication with a source of said fluid and a second inlet end joined with said fluid inlet port;
   a fluid outlet line having two ends, a first outlet end in fluid communication with said source of said fluid and a second outlet end joined with said fluid outlet port;
   means positioned across said inlet or outlet line for regulating the flow rate of fluid through said flowpath; and
   means for driving said fluid through said flowpath.

2. A device for therapeutically treating a desired portion of the body of a patient as recited in claim 1 further comprising means positioned in said inlet or outlet line for measuring the temperature of cooling fluid in said outlet line.

3. A device for therapeutically treating a desired portion of the body of a patient as recited in claim 2 wherein said temperature measuring means is a liquid thermometer.

4. A device for therapeutically treating a desired portion of the body of a patient as recited in claim 2 further comprising a housing containing said temperature measuring means and flow rate regulating means.

5. A device for therapeutically treating a desired portion of the body of a patient as recited in claim 1 wherein said flow rate regulating means is an in-line restriction valve.

6. A device for therapeutically treating a desired portion of the body of a patient as recited in claim 5 wherein said in-line restriction valve is manually operable.

7. A device for therapeutically treating a desired portion of the body of a patient as recited in claim 1 further comprising a pair of inlet and outlet couplings across each said second inlet and outlet ends and said inlet and outlet ports respectively, rendering said second ends dissociable from said inlet and outlet ports respectively.

8. A device for therapeutically treating a desired portion of the body of a patient as recited in claim 7 wherein said couplings are slidably disengagable.

9. A device for therapeutically treating a desired portion of the body of a patient as recited in claim 1 further comprising a power line connecting said drive means to an external power source.

10. A device for therapeutically treating a desired portion of the body of a patient as recited in claim 4 further comprising a continuous covering surrounding said inlet and outlet lines.

11. A device for therapeutically cooling a desired portion of the body of a patient comprising:
    a pad positionable on the desired portion of the body, said pad having a cooling fluid inlet port, a cooling fluid outlet port, and a continuous cooling fluid flowpath formed through said pad from said inlet port to said outlet port;
    a cooling fluid reservoir;
    a cooling fluid maintainable in said cooling fluid reservoir and circulatable through said flowpath;
    a cooling fluid inlet line having two ends, a first inlet end positionable in said fluid reservoir and a second inlet end joined with said cooling fluid inlet port;
    a cooling fluid outlet line having two ends, a first outlet end positionable in said fluid reservoir and a second outlet end joined with said cooling fluid outlet port;
    means for measuring the temperature of said cooling fluid in said outlet line;
    means for regulating the flow rate of fluid through said flowpath in response to the temperature of said cooling fluid in said outlet line; and
    a pump submersed in said cooling fluid maintained within said reservoir for driving said cooling fluid from said reservoir through said flowpath and said inlet and outlet lines.

12. A device for therapeutically cooling a desired portion of the body of a patient as recited in claim 11 wherein said temperature measuring means is a liquid thermometer positioned in said outlet line.

13. A device for therapeutically cooling a desired portion of the body of a patient as recited in claim 11 wherein said flow rate regulating means is an in-line restriction valve positioned across said inlet or outlet line.

14. A device for therapeutically cooling a desired portion of the body of a patient as recited in claim 13 wherein said in-line restriction valve is manually operable.

15. A device for therapeutically cooling a desired portion of the body of a patient as recited in claim 11 further comprising a pair of inlet and outlet couplings across each said second inlet and outlet ends and said inlet and outlet ports respectively, rendering said second ends dissociable from said inlet and outlet ports respectively.

16. A device for therapeutically cooling a desired portion of the body of a patient as recited in claim 11 further comprising a power line connecting said pump to an external power source.

17. A device for therapeutically cooling a desired portion of the body of a patient as recited in claim 11 further comprising a continuous covering surrounding said inlet and outlet lines.

18. A device for therapeutically cooling a desired portion of the body of a patient as recited in claim 11 further comprising a housing containing said temperature measuring means and flow rate regulating means.

19. A device for therapeutically cooling a desired portion of the body of a patient comprising:
    a pad positionable on the desired portion of the body, said pad having a cooling fluid inlet port, a cooling fluid outlet port, and a continuous cooling fluid flowpath formed through said pad from said inlet port to said outlet port;
    a cooling fluid reservoir;
    a cooling fluid maintainable in said cooling fluid reservoir and circulatable through said flowpath;
    a cooling fluid inlet line having two ends, a first inlet end positionable in said fluid reservoir and a second inlet end joined with said cooling fluid inlet port;
    a cooling fluid outlet line having two ends, a first outlet end freely positionable in said fluid reservoir and a second outlet end joined with said cooling fluid outlet port;
    a continuous insulative sheath covering said inlet and outlet lines;
    a pair of inlet and outlet couplings across each said second inlet and outlet ends and said inlet and outlet ports respectively, rendering said second ends dissociable from said inlet and outlet ports respectively;
    a thermometer positioned in said outlet line for measuring the temperature of said cooling fluid therein;
    a restriction valve positioned across said inlet or outlet line and having a manually operable control knob for regulating the flow rate of fluid through said flowpath in response to the temperature of said cooling fluid in said outlet line; and
    a pump connected to said first inlet and submersed in said cooling fluid maintained within said reservoir for driving said cooling fluid from said reservoir through said flowpath and said inlet and outlet lines.

* * * * *

REEXAMINATION CERTIFICATE (3803rd)

United States Patent [19]
Mason et al.

[11] B1 5,241,951
[45] Certificate Issued *Jul. 6, 1999

[54] THERAPEUTIC NONAMBIENT TEMPERATURE FLUID CIRCULATION SYSTEM

[75] Inventors: Bradley R. Mason, Olivenhain; Jeffrey T. Mason, Escondido, both of Calif.

[73] Assignee: Breg, Inc., Vista, Calif.

Reexamination Request:
No. 90/004,445, Nov. 5, 1996

Reexamination Certificate for:
Patent No.: 5,241,951
Issued: Sep. 7, 1993
Appl. No.: 07/767,494
Filed: Sep. 30, 1991

[ * ] Notice: This patent is subject to a terminal disclaimer.

Related U.S. Application Data

[63] Continuation-in-part of application No. 07/578,508, Sep. 5, 1990, Pat. No. 5,080,089.

[51] Int. Cl.[6] ............................................. A61H 9/00
[52] U.S. Cl. ................................... 607/104; 607/108
[58] Field of Search ................................. 607/104, 108

[56] References Cited

U.S. PATENT DOCUMENTS

| | | |
|---|---|---|
| 2,726,658 | 12/1955 | Chessey . |
| 3,744,555 | 7/1973 | Fletcher et al. . |
| 3,871,381 | 3/1975 | Roslonski . |
| 3,995,621 | 12/1976 | Fletcher et al. . |
| 4,026,299 | 5/1977 | Sauder et al. . |
| 4,170,998 | 10/1979 | Sauder . |
| 4,691,762 | 9/1987 | Elkins et al. . |
| 4,821,354 | 4/1989 | Little . |
| 4,844,072 | 7/1989 | French et al. . |
| 5,051,562 | 9/1991 | Bailey et al. . |
| 5,241,951 | 9/1993 | Mason et al. . |

*Primary Examiner*—Robert L. Nasser

[57] ABSTRACT

A device is provided for therapeutically treating a desired region of a patient's body with a nonambient temperature flluid which is circulated through a pad having a tortuous fluid pathway which is positioned on the treatment region. The device has fluid inlet and outlet lines, each having an end connected to the pad and an opposite end positioned in a reservoir containing the nonambient temperature fluid, thereby providing fluid communication between the pad and the reservoir, and enabling continuous circulation of the fluid therebetween. Fluid drive is provided by a submersible pump at the end of the fluid inlet line in the reservoir. Temperature control of the pad is enabled by an in-line valve and temperature monitor positioned in the outlet line.

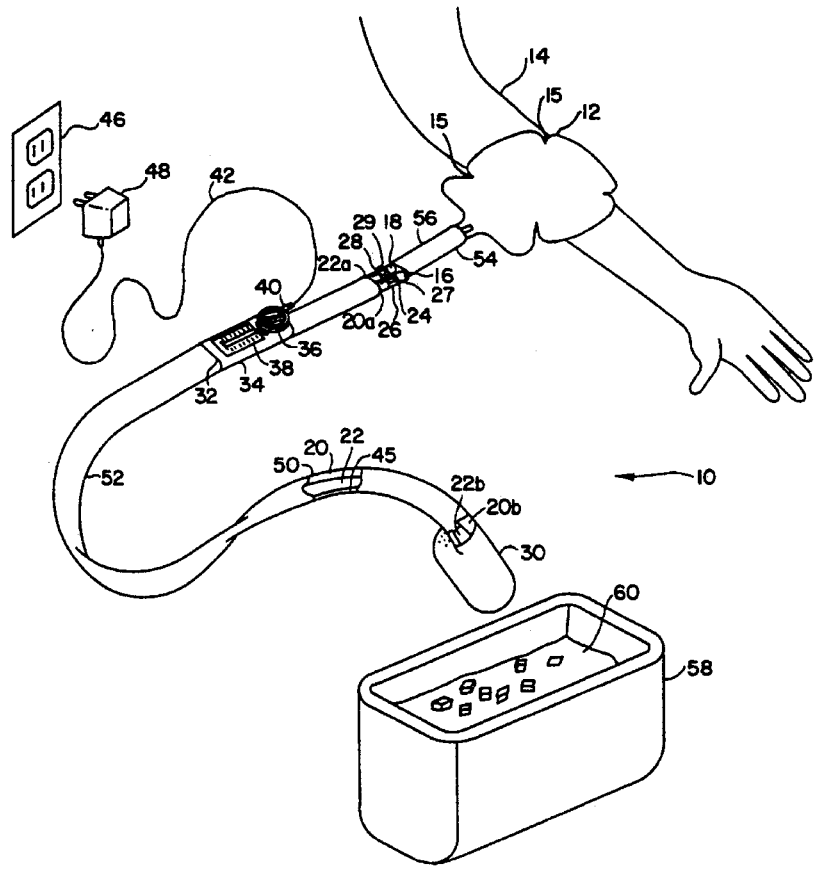

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 11–19 is confirmed.

Claims 1–4 and 10 are determined to be patentable as amended.

Claims 5–9, dependent on an amended claim, are determined to be patentable.

New claims 20–32 are added and determined to be patentable.

1. A device for therapeutically treating a desired portion of the body of a patient with a nonambient temperature fluid comprising:
   a pad positionable on the desired portion of the body, said pad having a fluid inlet port, a fluid outlet port, and a continuous fluid flowpath through said pad from said inlet port to said outlet port for circulation of a nonambient temperature fluid;
   a fluid inlet line having two ends, a first inlet end in fluid communication with a source of said fluid and a second inlet end joined with said fluid inlet port;
   a fluid outlet line having two ends, a first outlet end in fluid communication with said source of said fluid and a second outlet end joined with said fluid outlet port;
   *means for measuring the temperature of said fluid;*
   means positioned across said inlet or outlet line for regulating the flow rate of fluid through said flowpath *in response to the temperature of said fluid determined by said temperature measuring means;* and
   means for driving said fluid through said flowpath.

2. A device for therapeutically treating a desired portion of the body of a patient as recited in claim 1 [further comprising] *wherein said temperature measuring* means *is* positioned in said inlet or outlet line [for measuring the temperature of cooling fluid in said outlet line].

3. A device for therapeutically treating a desired portion of the body of a patient as recited in claim [2] *1* wherein said temperature measuring means is a liquid thermometer.

4. A device for therapeutically treating a desired portion of the body of a patient as recited in claim [2] *1* further comprising a housing containing said temperature measuring means and flow rate regulating means.

10. A device for therapeutically treating a desired portion of the body of a patient as recited in claim [4] *1* further comprising a continuous covering surrounding said inlet and outlet lines.

20. *A device for therapeutically treating a desired portion of the body of a patient as recited in claim 1 wherein said temperature measuring means is positioned in said outlet line for measuring the temperature of cooling fluid in said outlet line.*

21. *A device for therapeutically treating a desired portion of the body of a patient comprising:*
   *a pad positionable on the desired portion of the body, said pad having a fluid inlet port, a fluid outlet port, and a continuous fluid flowpath formed through said pad from said inlet port to said outlet port for circulation of a nonambient temperature fluid;*
   *an insulated fluid reservoir for passively substantially maintaining the nonambient temperature of said fluid in the absence of an active heating or cooling means in said device;*
   *a fluid inlet line having two ends, a first inlet end in fluid communication with said fluid reservoir and a second inlet end joined with said fluid inlet port;*
   *a fluid outlet line having two ends, a first outlet end in fluid communication with said fluid reservoir and a second outlet end joined with said fluid outlet port;*
   *a fluid inlet line having two ends, a first inlet end in fluid communication with a source of said fluid and a second inlet end joned with said fluid inlet port;*
   *a fluid outlet line having two ends, a first outlet end in fluid communication with said source of said fluid and a second outlet end joined with said fluid outlet port;*
   *means for measuring the temperature of said fluid;*
   *means positioned across said inlet or outlet line for regulating the flow rate of flluid through said flowpath in response to the temperature of said fluid determined by said temperature measuring means; and*
   *means for driving said fluid through said flowpath.*

22. *A device for therapeutically treating a desired portion of the body of a patient as recited in claim 21 wherein said temperature measuring means is positioned in said outlet line for measuring the temperature of cooling fluid in said outlet line.*

23. *A device for therapeutically treating a desired portion of the body of a patient as recited in claim 21 wherein said temperature measuring means is positioned in said inlet or outlet line.*

24. *A device for therapeutically treating a desired portion of the body of a patient as recited in claim 21 wherein said temperature measuring means is a liquid thermometer.*

25. *A device for therapeutically treating a desired portion of the body of a patient as recited in claim 21 further comprising a housing containing said temperature measuring means and flow regulating means.*

26. *A device for therapeutically treating a desired portion of the body of a patient as recited in claim 21 wherein said flow rate regulating means is an in-line restriction valve.*

27. *A device for therapeutically treating a desired portion of the body of a patient as recited in claim 26 wherein said in-line restriction valve is manually operable.*

28. *A device for therapeutically treating a desired portion of the body of a patient as recited in claim 21 further comprising a pair of inlet and outlet couplings across each said second inlet and outlet ends and said inlet and outlet* ports respectively, rendering said second ends dissociable from said inlet and outlet ports respectively.

29. A device for therapeutically treating a desired portion of the body of a patient as recited in claim 28 wherein said couplings are slidably disengageable.

30. A device for therapeutically treating a desired portion of the body of a patient as recited in claim 21 further comprising a power line connecting said drive means to an external power source.

31. A device for therapeutically treating a desired portion of the body of a patient as recited in claim 21 further comprising a continuous covering surrounding said inlet and outlet lines.

32. A device for therapeutically treating a desired portion of the body of a patient as recited in claim 21 wherein said drive means is a submersible pump positioned in said fluid reservoir.

* * * * *